(12) United States Patent
Tabron et al.

(10) Patent No.: US 11,154,451 B2
(45) Date of Patent: *Oct. 26, 2021

(54) COMPRESSION DEVICE FOR THE FOOT

(71) Applicant: SWELLING SOLUTIONS, INC., Minneapolis, MN (US)

(72) Inventors: Ian Stewart Tabron, Frodsham (GB); Wayne Lee Bonnefin, Chester (GB); Patrick Gerard Linnane, Ellesmere (GB); Anders Lennart Boström, Ekerö (SE)

(73) Assignee: Swelling Solutions, Inc., Minneapolis, MN (US)

(*) Notice: Subject to any disclaimer, the term of this patent is extended or adjusted under 35 U.S.C. 154(b) by 1030 days.

This patent is subject to a terminal disclaimer.

(21) Appl. No.: 15/288,279

(22) Filed: Oct. 7, 2016

(65) Prior Publication Data

US 2017/0020770 A1    Jan. 26, 2017

Related U.S. Application Data

(63) Continuation of application No. 14/068,647, filed on Oct. 31, 2013, now Pat. No. 9,463,135, which is a
(Continued)

(30) Foreign Application Priority Data

Jun. 8, 2005 (GB) .................................... 0511667
Nov. 17, 2005 (GB) .................................... 0523436

(51) Int. Cl.
*A61H 9/00* (2006.01)
*A61F 5/01* (2006.01)

(52) U.S. Cl.
CPC ............. *A61H 9/0078* (2013.01); *A61F 5/01* (2013.01); *A61F 5/012* (2013.01); *A61F 5/0127* (2013.01);
(Continued)

(58) Field of Classification Search
CPC ............. A61H 9/0078; A61H 2205/12; A61H 2201/1642; A61H 2201/1409;
(Continued)

(56) References Cited

U.S. PATENT DOCUMENTS 866,934 A     9/1907  Katz
3,865,102 A   2/1975  Birtwell et al.
(Continued)

FOREIGN PATENT DOCUMENTS

EP    0705588 A1    4/1996
EP    0770368 A1    5/1997
(Continued)

OTHER PUBLICATIONS

International Search Report dated Apr. 19, 2007 in the Netherlands, Patent Application No. PCT/GB2006/002086 filed Jun. 8, 2006.
(Continued)

*Primary Examiner* — Quang D Thanh
(74) *Attorney, Agent, or Firm* — Mueting Raasch Group

(57) ABSTRACT

A compression device for the foot including a wrap adapted to surround the foot, the wrap including at least two bladders which when inflated conform to the shape of the foot to provide compression, the bladders being positioned on the wrap so that a first bladder focuses compression on the heel of the foot and a second bladder focuses compression on the arch of the foot; a channel attached to each bladder for independently delivering fluid to each bladder; and a controller attached to the channels that generates and independently controls the flow of fluid to the bladders.

23 Claims, 5 Drawing Sheets

Related U.S. Application Data continuation of application No. 11/423,099, filed on Jun. 8, 2006, now Pat. No. 8,574,180.

(52) U.S. Cl.
CPC ............. *A61H 2201/0103* (2013.01); *A61H 2201/1409* (2013.01); *A61H 2201/1642* (2013.01); *A61H 2205/12* (2013.01)

(58) Field of Classification Search
CPC ........... A61H 2201/0103; A61F 5/0127; A61F 5/012; A61F 5/01
See application file for complete search history.

(56) References Cited

U.S. PATENT DOCUMENTS

| | | | |
|---|---|---|---|
| 3,999,220 A | 12/1976 | Keltner | |
| 4,029,087 A | 6/1977 | Dye et al. | |
| 5,022,387 A | 6/1991 | Hasty | |
| 5,117,812 A | 6/1992 | McWhorter | |
| 5,263,473 A | 11/1993 | McWhorter | |
| 5,383,894 A | 1/1995 | Dye | |
| 5,443,440 A | 8/1995 | Tumey et al. | |
| 5,449,379 A | 9/1995 | Hadtke | |
| 5,575,762 A | 11/1996 | Peeler et al. | |
| 5,626,556 A | 5/1997 | Tobler et al. | |
| 5,653,244 A | 8/1997 | Shaw et al. | |
| 5,769,801 A | 6/1998 | Tumey et al. | |
| 5,839,139 A | 11/1998 | Fink | |
| 5,843,007 A | 12/1998 | McEwen et al. | |
| 5,876,359 A | 3/1999 | Bock et al. | |
| 5,906,206 A | 5/1999 | Shaw et al. | |
| 5,916,183 A | 6/1999 | Reid | |
| 5,918,602 A | 7/1999 | Shaw et al. | |
| 5,931,797 A | 8/1999 | Tumey et al. | |
| 5,951,502 A | 9/1999 | Peeler et al. | |
| 6,007,559 A | 12/1999 | Arkans | |
| 6,062,244 A | 5/2000 | Arkans | |
| 6,109,267 A | 8/2000 | Shaw et al. | |
| 6,123,681 A | 9/2000 | Brown | |
| 6,135,116 A * | 10/2000 | Vogel | A61F 13/069 128/898 |
| 6,198,204 B1 | 3/2001 | Pottenger | |
| 6,203,510 B1 | 3/2001 | Takeuchi et al. | |
| 6,231,532 B1 | 5/2001 | Watson et al. | |
| 6,254,554 B1 | 7/2001 | Turtzo | |
| 6,290,662 B1 | 9/2001 | Morris et al. | |
| 6,296,617 B1 | 10/2001 | Peeler et al. | |
| 6,338,723 B1 | 1/2002 | Carpenter et al. | |
| 6,355,008 B1 | 3/2002 | Nakao | |
| 6,358,219 B1 | 3/2002 | Arkans | |
| 6,440,093 B1 | 8/2002 | McEwen et al. | |
| 6,463,934 B1 | 10/2002 | Johnson, Jr. et al. | |
| 6,544,202 B2 | 4/2003 | McEwen et al. | |
| 6,558,338 B1 | 5/2003 | Wasserman | |
| 6,592,534 B1 | 7/2003 | Rutt et al. | |
| 6,620,116 B2 | 9/2003 | Lewis | |
| 6,656,141 B1 | 12/2003 | Reid | |
| 6,749,556 B2 | 6/2004 | Banik | |
| 6,846,295 B1 | 1/2005 | Ben-Nun | |
| 6,966,884 B2 | 11/2005 | Waldridge et al. | |
| 6,988,423 B2 | 1/2006 | Bolam et al. | |
| 7,001,384 B2 | 2/2006 | Berish et al. | |
| 7,056,297 B2 | 6/2006 | Dohno et al. | |
| 7,074,200 B1 | 7/2006 | Lewis | |
| 7,329,232 B2 | 2/2008 | Lipshaw et al. | |
| 7,354,410 B2 | 4/2008 | Perry et al. | |
| 7,442,175 B2 | 10/2008 | Meyer et al. | |
| 7,491,185 B2 | 2/2009 | Couvillon, Jr. | |
| 7,618,384 B2 | 11/2009 | Nardi et al. | |
| 7,637,879 B2 | 12/2009 | Barak et al. | |
| 7,637,922 B2 | 12/2009 | Johnson et al. | |
| 7,868,221 B2 | 1/2011 | Munch-Fals et al. | |
| 7,992,217 B2 | 8/2011 | Hyde et al. | |
| 8,029,451 B2 | 10/2011 | Meyer et al. | |
| 8,079,969 B2 | 12/2011 | Rousso et al. | |
| 8,079,970 B2 | 12/2011 | Meyer et al. | |
| 8,100,841 B2 | 1/2012 | Rousso | |
| 8,100,842 B2 | 1/2012 | Rousso | |
| 8,105,252 B2 | 1/2012 | Rousso | |
| 8,574,180 B2 * | 11/2013 | Tabron | A61F 5/01 601/148 |
| 9,463,135 B2 * | 10/2016 | Tabron | A61F 5/01 |
| 2001/0018564 A1 | 8/2001 | Manor et al. | |
| 2001/0056250 A1 | 12/2001 | Manor et al. | |
| 2002/0042583 A1 * | 4/2002 | Barak | A61H 9/0078 601/1 |
| 2003/0171703 A1 | 9/2003 | Grim et al. | |
| 2004/0073146 A1 | 4/2004 | Weintraub et al. | |
| 2004/0199090 A1 | 10/2004 | Sanders et al. | |
| 2004/0210176 A1 | 10/2004 | Diana | |
| 2005/0087251 A1 | 4/2005 | Sumitomo | |
| 2005/0143682 A1 * | 6/2005 | Cook | A61H 23/04 601/151 |
| 2005/0159690 A1 * | 7/2005 | Barak | A61H 9/0078 601/149 |
| 2005/0187503 A1 | 8/2005 | Tordella et al. | |
| 2006/0074362 A1 | 4/2006 | Rousso et al. | |
| 2006/0135894 A1 * | 6/2006 | G. Linnane | A61H 9/005 601/152 |
| 2006/0287672 A1 | 12/2006 | McEwen et al. | |
| 2007/0038167 A1 | 2/2007 | Tabron et al. | |
| 2007/0049852 A1 | 3/2007 | Linnane et al. | |
| 2007/0049853 A1 | 3/2007 | Adams et al. | |
| 2007/0135743 A1 * | 6/2007 | Meyer | A61H 9/0078 601/152 |
| 2008/0255494 A1 | 10/2008 | Rousso et al. | |
| 2009/0018474 A1 | 1/2009 | Nakao | |
| 2009/0076424 A1 | 3/2009 | Sim et al. | |
| 2009/0118651 A1 | 5/2009 | Rousso et al. | |
| 2010/0010404 A1 | 1/2010 | Nardi et al. | |
| 2010/0010406 A1 | 1/2010 | Nardi et al. | |
| 2010/0036299 A1 | 2/2010 | Gough | |
| 2010/0204803 A1 | 8/2010 | Tozzi et al. | |
| 2011/0009795 A1 | 1/2011 | Graham et al. | |
| 2011/0066093 A1 | 3/2011 | Vess | |
| 2011/0082401 A1 | 4/2011 | Iker et al. | |
| 2011/0125183 A1 | 5/2011 | Lipshaw et al. | |
| 2011/0131839 A1 | 6/2011 | Ballin et al. | |
| 2011/0196269 A1 | 8/2011 | Arkans | |
| 2011/0245743 A1 | 10/2011 | Eddy | |

FOREIGN PATENT DOCUMENTS

| | | | |
|---|---|---|---|
| EP | 1018329 B1 | 4/2004 | |
| EP | 1895954 B1 | 4/2004 | |
| EP | 1893143 B1 | 1/2010 | |
| GB | 866934 | 5/1961 | |
| JP | 200517217 A | 12/2000 | |
| JP | 2001293055 A | 10/2001 | |
| WO | WO 95/03016 A1 | 2/1995 | |
| WO | WO 9808470 A1 | 3/1998 | |
| WO | WO 00/06077 A2 | 2/2000 | |
| WO | WO 2005/007060 A2 | 1/2005 | |
| WO | WO 2006/131733 A1 | 12/2006 | |
| WO | WO 2006/131740 A2 | 12/2006 | |
| WO | WO 2011/022305 A2 | 2/2011 | |

OTHER PUBLICATIONS

International Search Report dated Jun. 13, 2007 in the Netherlands, Patent Application No. PCT/GB2006/002097 filed Jun. 8, 2006.
International Preliminary Report on Patentability dated Dec. 11, 2007, in Switzerland, Patent Application No. PCT/GB2006/002086 filed Jun. 8, 2006.
Written Opinion International dated Dec. 11, 2007, in Netherlands, Patent Application No. PCT/GB2006/002086 filed Jun. 8, 2006.
International Preliminary Report on Patentability dated Dec. 11, 2007, in Switzerland, Patent Application No. PCT/GB2006/002097 filed Jun. 8, 2006.

(56) References Cited

OTHER PUBLICATIONS

Written Opinion International dated Dec. 11, 2007, in Netherlands, Patent Application No. PCT/GB2006/002097 filed Jun. 8, 2006.

* cited by examiner

COMPRESSION DEVICE FOR THE FOOT

This application is a continuation of U.S. application Ser. No. 14/068,647, filed Oct. 31, 2013, which is a continuation of U.S. application Ser. No. 11/423,099, filed Jun. 8, 2006 (now U.S. Pat. No. 8,574,180), which claims priority to United Kingdom Application No. GB0511667.8, filed Jun. 8, 2005, and United Kingdom Application No. GB0523436.4, filed Nov. 17, 2005, all of which are herein incorporated by reference in their entirety.

This invention relates to a compression device for the limb and particularly to a device for use on the foot. The device is particularly suited for use in the type of compression therapy used in the treatment of venous foot ulcers or venous heel ulcers.

BACKGROUND OF THE INVENTION

Various compression devices are known for applying compressive pressure to a patient's limb. These types of devices are used to assist mainly in the prevention of deep vein thrombosis (DVT), vascular disorders and the reduction of oedema. Prior art devices are adapted for use in a hospital setting in which they are used predominantly for the prevention of DVT in patients with a high risk for developing the same. U.S. Pat. Nos. 5,117,812, 5,022,387 and 5,263,473 (The Kendall Company), U.S. Pat. No. 6,231,532 (Tyco International Inc.), U.S. Pat. No. 6,440,093 (McEwen, et al.) and U.S. Pat. No. 6,463,934 (Aircast Inc.) disclose such devices.

Compression therapy is used in the treatment of venous leg ulcers. The treatment relies on the compression achieving a reduction in oedema and improved return of blood via the venous system. This in turn reduces the residence time for blood supplied to the lower limb and the severity of ischaemic episodes within the limb that can result in tissue breakdown.

Compression of the foot can be achieved by a pneumatic compression device. The known devices apply pressure to the foot and to the rest of the limb through a thick cuff which is large, bulky and powered mainly by electricity. The known devices not only affect patient mobility but are also aesthetically unacceptable to many patients. For instance the device can prevent the wearing of the patient's ordinary shoes and clothes meaning that the patient is housebound and unable to walk. In the hospital devices, these disadvantages are not apparent because the patient is largely confined to bed.

A problem in providing an aesthetically acceptable foot cuff is one of supplying the pneumatic fluid to the cuff. In the hospital devices of the prior art, pneumatic fluid is supplied to the cuffs through a network of pipes without consideration to the patient being mobile, wearing normal clothing or wearing a shoe. Even if the patient is able to put their shoe on with the cuff in place in a deflated state, the shoe may prevent inflation of the cuff in the areas where pressure is required as the shoe may block the path for the passage of pneumatic fluid. If a tube is used to supply the fluid to, for instance, the arch of the foot, the shoe may collapse or kink the tube and may cause pressure points on the foot.

In addition, a problem with the devices of the prior art is that the cuff is generally cylindrical and applies pressure over the whole of its surface to the foot, meaning that the mobility of the ankle is reduced making walking difficult even if the patient can wear a shoe and inflate the cuff.

Pneumatic compression devices do, however, have advantages in particular over compression bandages. They provide an effective treatment, while deflated, the inflatable cuff or cuffs are easy to apply to the patient's foot and the pressure is more readily controlled and monitored. Also, they are not subject to the effect of radius where the level of compression depends on the circumference of the limb so that high pressure and low pressure spots occur at the ankle where the radius under the bandage varies. The effect of radius is a fundamental limitation of elasticated bandages and stockings. In addition, it is difficult to apply pressure to the heel of the foot with an elastic bandage and this is an area in which ulcers occur. With elastic bandages, applying pressure to the heel means that mobility in the ankle is reduced as the bandage applies pressure over the whole ankle. This reduction in mobility impairs venous return as the patient is unable to walk normally.

There, thus, exists a need for a foot cuff, which focuses the pressure applied by the cuff to those areas where ulcers are prevalent and limits inflation of the cuff in the surrounding areas so that the patient is able to wear their ordinary shoes and clothes with the cuff inflated. There is also a need for a means of supplying pneumatic fluid to a foot cuff so that inflation is focused on certain areas and the patient is allowed to be mobile and wear ordinary shoes without interrupting the supply of fluid to the cuff. There is also a need for a foot cuff that enables the application of pressure in a manner that is flexible enough to allow the treatment of various indications from one device.

SUMMARY OF THE INVENTION

We have now invented a device for applying compression against a patient's foot which alleviates the above problems by providing a device which is simple to apply to the foot, focuses pressure on certain areas of the foot, is low profile and lightweight and has a discreet pneumatic fluid supply. A first aspect of the present invention provides a compression device for the foot comprising:

a wrap adapted to surround the foot, the wrap comprising at least two bladders which when inflated conform to the shape of the foot to provide compression, the bladders being positioned on the wrap so that a first bladder focuses compression on the heel of the foot and a second bladder focuses compression on the arch of the foot;

a channel attached to each bladder for independently delivering fluid to each bladder; and a controller attached to the channels that generates and independently controls the flow of fluid to the bladders.

We have found that such a device may bring the advantages of applying pressure to the heel and arch of the patient without reducing mobility. The pressure can also be targeted on the area of the heel where ulcers are most prevalent. Independent supply and control of fluid to two bladders means that the device can be operated in a number of ways. This flexibility enables a range of treatments to be provided by the device and, thus, allows one device to treat a number of different indications.

The device may be operated so that the pressures applied by the heel and arch bladders may be the same as or different from each other or may be the same or different to the pressures applied by an associated device. The heel bladder, for example, may be at the same pressure as bladders located in an associated leg sleeve and may be attached thereto.

Preferably, the controller comprises a microprocessor control system and a pump. More preferably, the device comprises at least one pressure sensor in the channel or positioned in the device, the sensors providing readings of the pressure experienced by the foot due to the inflation of the wrap by the controller.

DETAILED DESCRIPTION OF THE INVENTION

Figure 1:
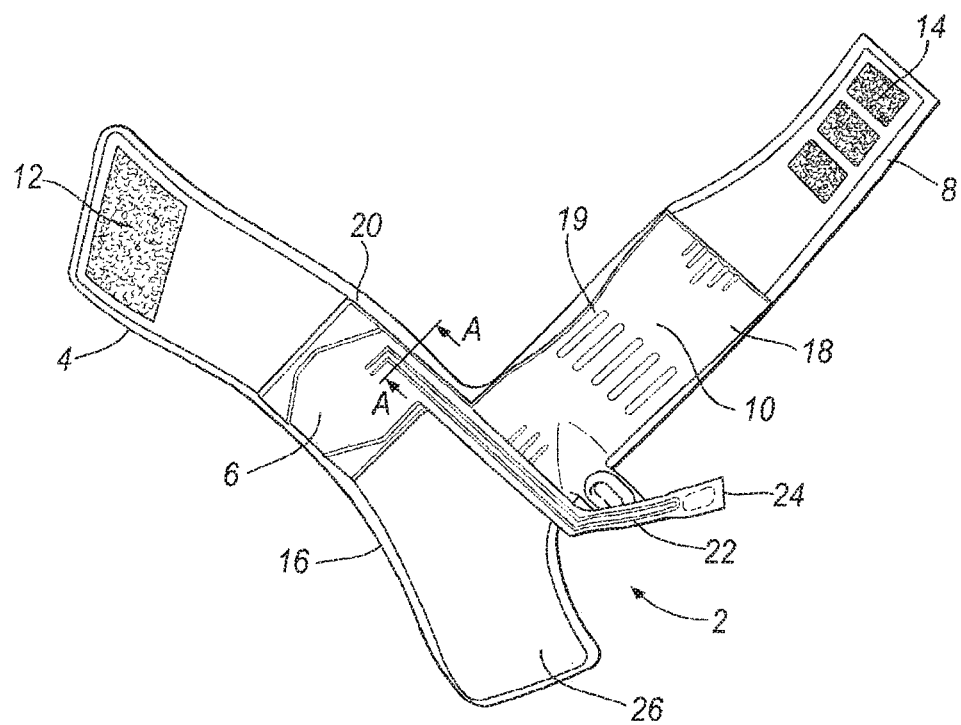
FIG. 1 is a plan view of the wrap of one embodiment of the present invention.

The wrap comprises two or more individually inflatable bladders. The bladders may be formed from an outer wall and an inner wall, the inner wall contacting the foot in use. The wrap may comprise an inelastic fabric to which the bladders are fixed or the fabric may form the outer wall of the bladder. Preferably, the bladder walls are elastic and are joined to the wrap by welding.

Preferably the bladder is provided with means to separate the walls in use to maintain a path for fluid flow into and out of the bladder. This has the advantage that the inflation of the bladder may be localized to the area of the foot where pressure needs to be applied, for instance, the heel and the arch of the foot, and may be limited in those areas where pressure need not be applied, for instance, the sides of the foot. In this way the patient is able to be mobile, has mobility in the ankle and may wear their ordinary clothes and shoes.

The separation means in the bladder may be an open foam material positioned between the bladder walls or may be a spacer provided on the interior of at least one bladder wall. By this means it is not necessary to have a tube supplying fluid running into the patient's shoe and causing possible pressure points or blockages. The spacer is preferably made from a flexible material that is relatively incompressible and is elongate to create a channel for the supply of fluid into and out of the bladder.

Preferably, the wrap has a Y-shaped outline when in an unwrapped state. One arm of the Y is provided with a bladder to apply pressure to the heel of the foot in use and the other arm of the Y is provided with a bladder to apply pressure to the arch of the foot when in use. The Y-shaped wrap may be opened to a flat state making application to the patient's foot easy enough that the patient may apply the device unaided.

The wrap may be applied to the foot by the patient placing the arch of their foot on the arch bladder located on one arm of the Y (the arch arm) and with their heel in the fork of the Y. The tail of the Y may then be wrapped over the top of the foot and the other arm of the Y (the heel arm) wrapped around the heel and fixed to the tail by loop and hook fastening. The free end of the arch arm is then folded over the top of the foot and attached to the heel arm and tail of the Y by hook and loop fastenings. Preferably the heel and arch bladders are located close to the junction of the arms.

Alternatively, in another embodiment, the wrap may comprise a one strap fastening, fastened over the top of the foot, the heel and arch parts of the wrap being integral. The foot may be inserted in such a device and the strap fastened over the instep.

The heel bladder is preferably divided into two parts which may be connected and provides pressure in the areas between the malleoli and the achilles on either side of the heel. This bladder can be permanently fixed in position on the wrap or can be repositionable to customise the fit to individual patients.

The wrap may be used in conjunction with a compression sleeve for the lower limb such as that described in GB 0307097.6 or GB 0423410.0. When such a sleeve is present the wrap may be integral with it or be connectable to it. The pressures applied by the heel and arch bladders may be the same or different from each other or may be the same or different to the pressures in the cuffs of the sleeve.

The heel and/or arch bladders can connect directly to the controller that generates and controls the flow of fluid in the sleeve or can connect to one of the bladders in the sleeve and, thus, be at the same pressure as that bladder or at different pressures.

Preferably, the channels connecting the heel and arch bladders to the sleeve or controller are low in profile and resistant to crushing or kinking for instance by the wearer's shoe. The channels may have a similar construction to the bladder and comprise an outer wall and an inner wall in the form of elongate strips provided with means to separate the walls in use to create a path for fluid flow from the sleeve or controller. In this way the separating means maintain a path for fluid flow despite crushing or kinking of the channel. The separation means in the channel can be the same as that used in the bladder and, preferably, is an elongate flexible strip, narrower than the width of the channel walls.

The channel walls are, preferably, made of the same material as the bladders and may be welded to a window in the bladder wall of the sleeve or wrap or cuff to make an air tight connection.

Preferably, there are one or more individual sensors associated with each bladder to monitor the pressure from that bladder. This allows the controller to precisely control the pressure in that bladder and the device to comply with a predetermined pressure profile.

In a second embodiment, the invention provides a cuff for providing compression to a limb, the cuff comprising an outer wall joined to an inner wall to form a bladder, the bladder being provided with a spacer to separate the walls to create a channel for fluid to flow into and out of the bladder.

The advantage of the cuff of the invention is that the separating means allow the bladders to be shaped so that the compression generated by the device can be focused on those areas where ulcers are more prevalent without compromising the path for fluid movement.

The spacer is made from a relatively incompressible material that spaces the walls apart but does not allow the bladder or channel to become obstructed in the manner that a tube may become obstructed by kinking or collapsing or being flattened against, for instance, a shoe.

Preferably, the bladder walls are selectively welded together so that inflation of the bladder is limited in the welded areas which can in use contact those parts of the foot where compression is not required, for example, the sides of the foot or over bony prominences in the heel.

The spacer is, preferably, provided on the inside of at least one wall of the bladder and, even more preferably, a spacer is provided on the inner wall of the bladder and a spacer is provided on the outer wall of the bladder which spacers abut when the bladder is deflated.

The spacers allow pneumatic fluid to flow into the bladders and have the advantage that they are easily constructed on the bladder walls. The spacers may be elongate and flexible so that the bladder may be shaped to provide an elongate channel for connection to a conduit of the device.

In a third embodiment, the invention provides a channel for connecting one or more bladders to each other or to a controller, the channel comprising an elongate outer wall joined to an elongate inner wall, the channel being provided with means to separate the was to create a path for fluid to flow into and out of the channel.

The separating means are preferably a spacer provided on at least one wall of the channel and even more preferably a spacer provided on the inner wall of the channel and a spacer provided on the outer wall of the channel which spacers abut when the channel is deflated.

Having spacers on opposing walls means that each spacer need only be half the thickness of a single spacer on one wall yet achieve the same separation of the walls. This makes the channel or bladder more flexible and, as the spacers can slide against each other, enables the bladder and channels to conform readily to curved surfaces.

The spacers are preferably made from the same material as the bladders or channels and are preferably about 4 mm wide and 0.4 mm thick and arranged in opposing pairs.

In FIG. 1 the wrap of the invention is shown open in plan view with the surface that will contact the foot in use uppermost. The wrap 2 is generally Y-shaped and comprises a first arm 4 provided with a bladder 6, which contacts the arch of the foot in use and a second arm 8 provided with a bladder 10, which contacts the heel of the foot in use. The first arm 4, the arch arm, is provided at its extremity with one part of the hook and loop fastening material 12. The second arm 8, the heel arm, is provided at its extremity with one part of a hook and loop fastening material 14. The heel bladder 10 and the arch bladder 6 are located close to the junction of the arms but may be repositionable on the wrap by the use of hook and loop fastening material.

Figure 7:
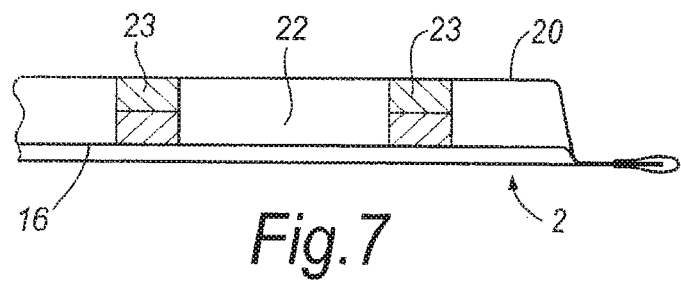
FIG. 7 is a cross sectional view taken on the line A-A of FIG. 1 showing the spacing means in the channel.

In the wrap of FIG. 1 the bladders 6, 10 are constructed from an outer wall, which is welded to the wrap and an inner wall 18, 20 welded to the outer wall. Pneumatic fluid, usually air, is supplied to the bladders through channels 22 formed by spacers 23 on both the inner and outer walls which abut when the bladder is in a deflated state, best seen in FIG. 7.

The channels 22 run across the fork in the Y and are terminated by a connector 24, which attaches to a conduit (not shown) and a control unit. Alternatively, the channels can be elongated further still and connect directly to the controller. The tail of the wrap 26 is provided on its outer surface with one part of a hook and loop fastening 28 best seen in FIG. 5.

Figure 2:
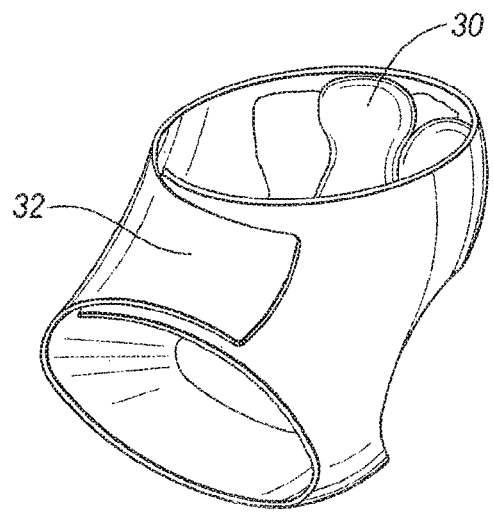
FIG. 2 is a perspective view of the heel part of another embodiment of the wrap of the invention.

FIG. 2 shows a single strap embodiment of the wrap of the present invention where the heel bladder 30 is integral with a strap 32, which fastens the device over the instep of the foot. The heel bladder 30 is in two connected parts so that pressure is applied by the bladder on either side of the posterior tibiofibular ligament. The separation of the bladder 30 into two parts may be achieved by a series of welds of the inner and outer walls of the bladder, as shown in FIG. 1 at 19. The welds are interspersed with spacers to provide a path for fluid flow. Similarly spacers can be provided in any region where a bladder or channel is likely to kink or block for instance over a bony prominence.

Figure 3:
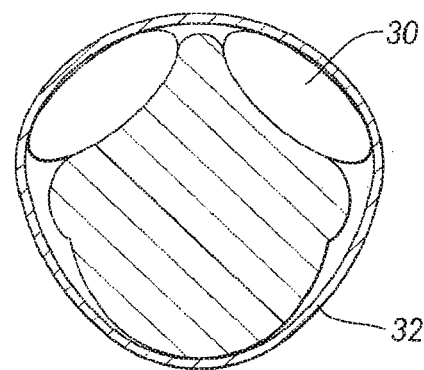
FIG. 3 is a cross-sectional view on a plane horizontally through the ankle of the patient and viewed from above with the device of FIG. 2 on the foot showing the position of the heel bladder.

In use, the heel bladder 30 applies pressure to the heel in the manner shown in FIG. 3. In FIG. 3, the heel bladder 30 is shown in an inflated state with pressure being applied on either side of the heel.

Figure 4:
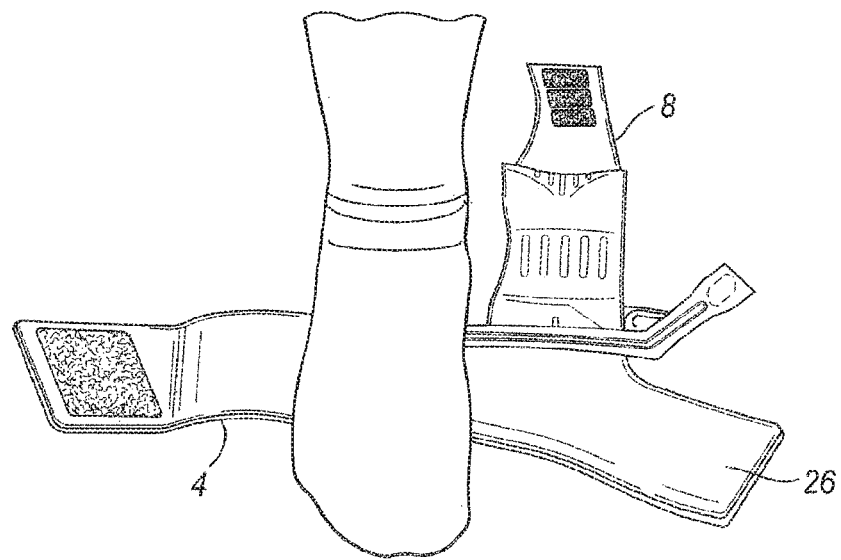
FIG. 4 is a perspective view of the first stage of applying the wrap of FIG. 1 to a foot.
Figure 5:
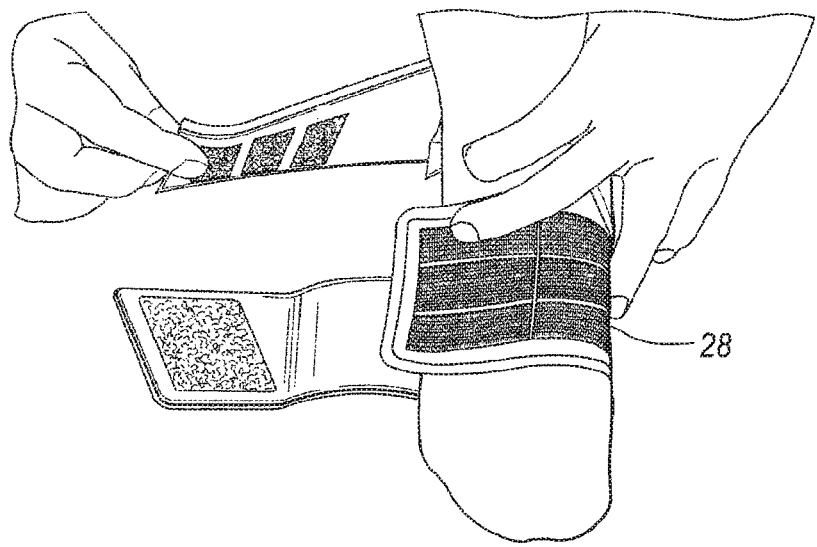
FIG. 5 is a perspective view of the second stage of applying the wrap of FIG. 1 to a foot.
Figure 6:
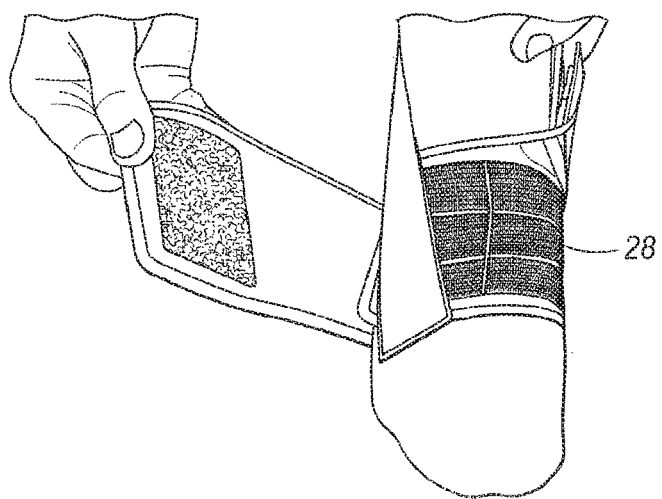
FIG. 6 is a perspective view of the final stage of applying the wrap of FIG. 1 to a foot.

FIGS. 4, 5 and 6 show the application of the wrap of FIG. 1 to the foot of a patient. FIG. 4 shows the first stage of application where the patient places the arch of their foot over the arch bladder 6, the heel being positioned in the fork of the Y. FIG. 5 shows the second stage of application where the tail of the Y 26 is wrapped over the instep of the foot and the heel arm 8 is lifted up and around the heel of the foot so that the fastening 14 comes into contact with the fastening 28 on the outer surface of the tail 26. FIG. 6 shows the final stage in applying the wrap where the heel arm 4 is folded over the foot to bring the fastening 12 in contact with the fastening 28.

FIG. 6 also shows the positioning of the connector 24 and channels 22 at the top of the foot, which allows the conduit to be attached to the wrap without a tube having to be run down the side of the foot to the arch bladder 6 and without a tube having to be run around the edge of the foot to the heel bladder 10. The channels 22 create a reliable passage of fluid to the bladders 6, 10 without causing pressure points, without the risk of a tube that kinks or collapses, and discreetly, so that a network of tubes is not apparent to others. The channels 22 also allow the patient to wear their ordinary shoes.

The wrap of FIG. 1 allows the patient mobility in their ankle, as the device does not restrict hinge or rotational movement of the ankle.

Figure 8:
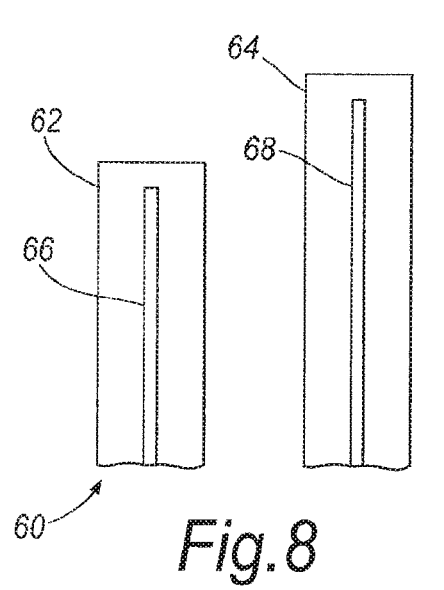
FIGS. 8, 9 and 10 are perspective views of a low profile air channel according to another embodiment of the invention and in particular showing the connection of a channel to a bladder.
Figure 9:
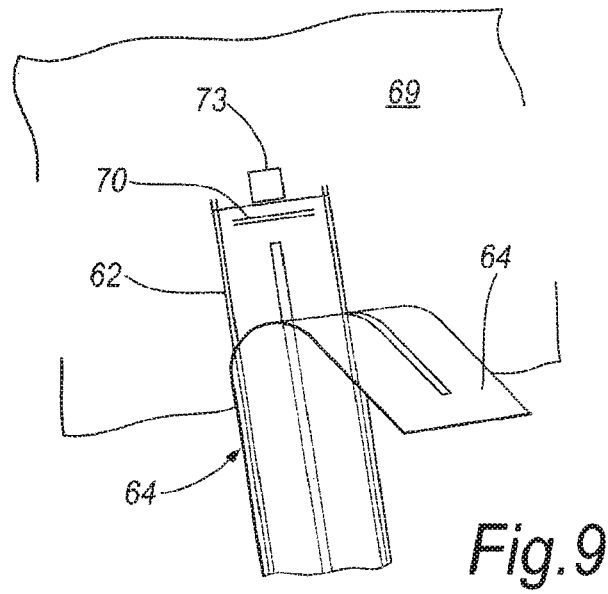
Figure 10:
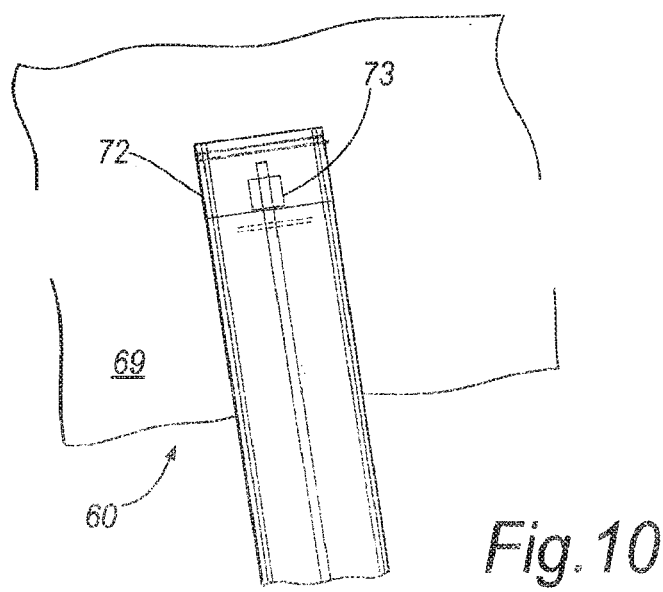
Figure 11:
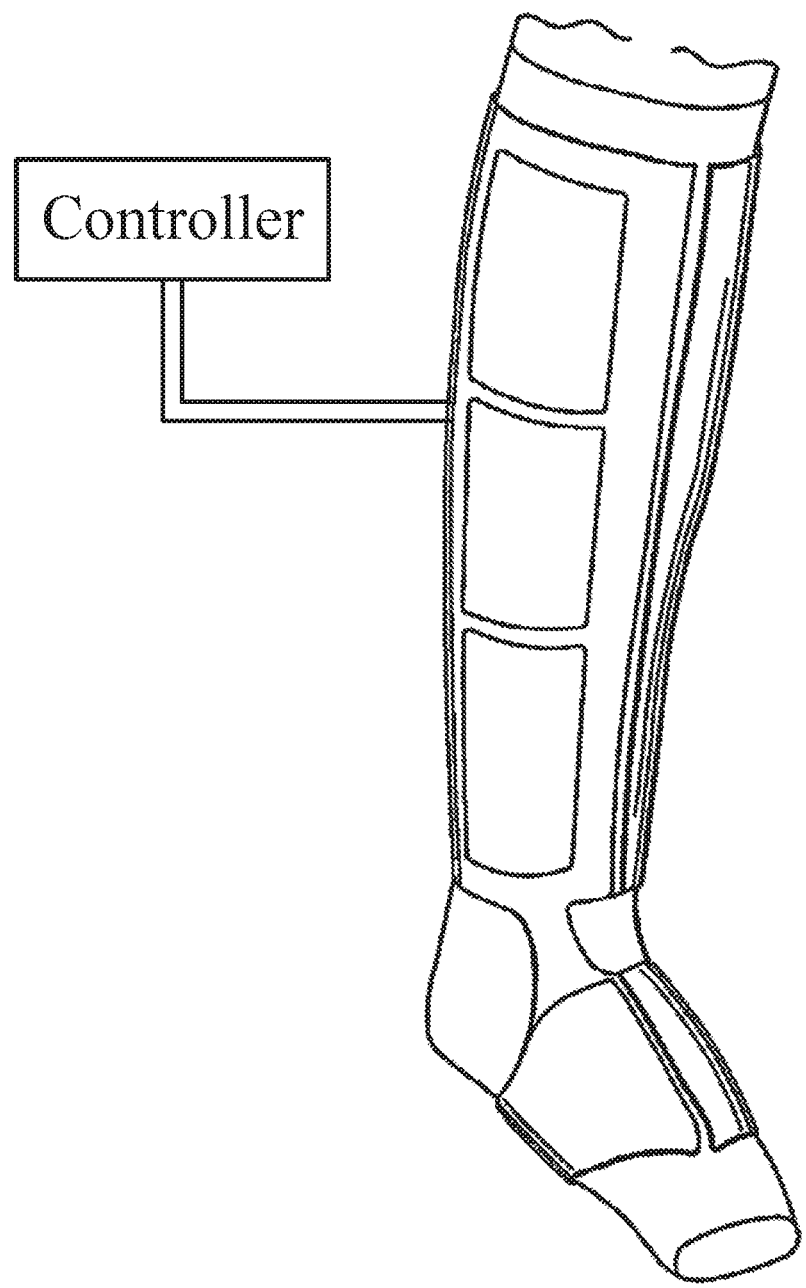
FIG. 11 is a perspective view of a compression sleeve integral with a wrap.

FIGS. 8, 9 and 10 show an embodiment of the invention in the form of an elongate channel 60 where the channel walls 62, 64 are each provided with a spacing strip 66, 68 attached to the inner surface of each wall so that they abut when the walls 62, 64 are welded together on their long sides to form the channel 60. The channel 60 provides a lower profile and is more discrete than a conventional tube. The lower profile means that the flat channel will not create pressure points against the patient's limb, when for instance a shoe is worn.

To join the channel 60 to bladder wall 69, the wall 62 is made shorter than wall 64 as shown in FIG. 8 so that when the walls are welded together to form channel 60 part of wall 64 and strip 68 is left exposed. The channel wall 64, is folded back at its top edge to expose the channel interior as shown in FIG. 9. The channel wall 62 is placed on the bladder wall 69 under opening 73 and welded along its upper edge 70 to the bladder wall 69. The channel wall 64 is folded up over the opening 73 in bladder wall 69 and welded in place around its free edges shown as lines 72 in FIG. 10. The welded connection of the air channel 60 to bladder wall 69 provides a more secure fluid connection than the use of conventional tubing and air connectors.

Although the present invention has been shown and described with respect to several preferred embodiments thereof, various changes, omissions and additions to the form and detail thereof may be made without departing from the spirit and scope of the invention.

We claim:

1. A compression device for a lower limb terminating in a foot, wherein the foot extends from a heel to toes at a distal end of the foot, the heel having a plantar portion at a bottom of the foot and a posterior portion at a back of the foot, wherein the foot further includes an arch and a ball of the foot more distal than a distal end of the arch, the compression device comprising:
   a compression sleeve for a portion of the lower limb from which the foot extends comprising one or more bladders for applying pressure to the portion of the lower limb;
   a wrap integral with the compression sleeve and adapted to surround one or more portions of the foot, the wrap comprising at least two bladders which when inflated conform to a shape of the one or more portions of the foot to provide compression, wherein the wrap comprises an inner wall and an outer wall that form the at least two bladders, wherein the wrap when in use comprises at least a first portion wrapped around the foot and covering at least the arch of the foot and a second portion positioned so that a first bladder portion of the at least two bladders focuses compression on a first part of the posterior portion of the heel of the foot and a second bladder portion of the at least two bladders focuses compression on a second part of the posterior portion of the heel of the foot, wherein the first bladder portion is separated from the second bladder portion by welds between the inner and outer walls, wherein the wrap is devoid of material forming the wrap at an open area so that the user places the plantar portion of the heel at the bottom of the foot in the open area when the wrap is being applied to the foot such that the wrap does not cover at least a part of the plantar portion at the bottom of the heel, and wherein the wrap is configured such that the wrap does not cover the ball of the foot when the wrap is applied to the foot;
   a channel attached to each bladder of the at least two bladders and the one or more bladders for delivering fluid to each bladder of the at least two bladders and the one or more bladders; and
   a controller attached to the channels that controls the flow of the fluid to the at least two bladders and the one or more bladders.

2. The compression device of claim 1, wherein the wrap is Y-shaped when in an unwrapped state.

3. The compression device of claim 2, wherein the first and second bladder portions are located on a first arm of the Y-shaped wrap and an arch bladder is located on a second arm of the Y-shaped wrap.

4. The compression device of claim 1, wherein the wrap comprises an inelastic fabric.

5. The compression device of claim 1, wherein at least one bladder of the at least two bladders comprises separation apparatus to separate the walls to create a path for fluid flow into and out of the at least one bladder.

6. The compression device of claim 1, wherein the inner and outer walls of at least one bladder of the at least two bladders are selectively welded to limit the inflation of the at least one bladder in certain areas so that the pressure applied by the at least one bladder is focused on selected areas of the foot.

7. The compression device of claim 1, wherein the compression device further comprises at least one arch bladder positioned on the first portion of the wrap to focus compression on the arch of the foot.

8. The compression device of claim 1, wherein the first bladder portion and the second bladder portion provide compression on the posterior portion of the heel of the foot in the areas between malleoli and an Achilles tendon on either side of the heel, respectively.

9. The compression device of claim 1, wherein, when in use, at least one channel associated with the at least two bladders runs across at least a portion of the posterior portion of the heel between the first portion of the wrap and the second portion of the wrap.

10. A compression device for a lower limb terminating in a foot, wherein the foot extends from a heel to toes at a distal end of the foot, the heel having a plantar portion at a bottom of the foot and a posterior portion at a back of the foot, wherein the foot further includes an arch and a ball of the foot more distal than a distal end of the arch, the compression device comprising:
   a compression sleeve for a portion of the lower limb from which the foot extends comprising one or more bladders for applying pressure to the portion of the lower limb;
   a wrap integral with the compression sleeve and adapted to surround one or more portions of the foot, the wrap comprising at least a first portion adapted to be wrapped around the foot and configured to covering at least the arch of the foot and a second portion comprising at least one heel bladder to focus compression on the posterior portion of the heel of the foot, wherein the at least one heel bladder comprises a first bladder portion and a second bladder portion positioned when in use to provide compression on the posterior portion of the heel of the foot in the areas between malleoli and an Achilles tendon on either side of the heel, respectively, wherein bladder walls of the at least one heel bladder are selectively welded to separate the first bladder portion from the second bladder portion by selective welds, wherein the wrap is devoid of material forming the wrap at an open area so that the user places the plantar portion of the heel at the bottom of the foot in the open area when the wrap is being applied to the foot such that the wrap does not cover at least a part of the plantar portion at the bottom of the heel, and wherein the wrap is configured such that the wrap does not cover the ball of the foot when the wrap is applied to the foot;
   a channel attached to each bladder of the at least one heel bladder and the one or more bladders for delivering fluid to each bladder of the at least one heel bladder and the one or more bladders; and
   a controller attached to the channels that controls the flow of the fluid to the at least one heel bladder and the one or more bladders.

11. The compression device of claim 10, wherein the first portion of the wrap further comprises at least one arch bladder to focus compression on the arch of the foot.

12. The compression device of claim 10, wherein the at least one heel bladder is integral with a strap of the first portion of the wrap which fastens the wrap over an instep of the foot.

13. The compression device of claim 10, wherein the wrap is Y-shaped when in an unwrapped state.

14. The compression device of claim 10, wherein the at least one heel bladder comprises an outer wall joined to an inner wall which contacts the foot in use, the at least one heel bladder being provided with separation apparatus to separate the walls to create a path for fluid flow into and out of the at least one heel bladder.

15. The compression device of claim 14, wherein the separation apparatus comprises a spacer provided on the interior of at least one wall of the at least one bladder which separates the walls of the at least one bladder when the at least one bladder is deflated.

16. The compression device of claim 10, wherein the selective welds of the bladder walls limit the inflation of the at least one heel bladder in certain areas so that the pressure applied by the at least one heel bladder is focused on selected areas of the foot.

17. The compression device of claim 1, wherein the wrap does not extend to the toes at the distal end of the foot when the wrap is applied to the foot.

18. A compression device for a lower limb terminating in a foot, wherein the foot extends from a heel to toes at a distal end of the foot, the heel having a plantar portion at a bottom of the foot and a posterior portion at a back of the foot, wherein the foot further includes an arch and a ball of the foot more distal than a distal end of the arch, the compression device comprising:
  a first compression portion for a portion of the lower limb from which the foot extends comprising one or more bladders for applying pressure to the portion of the lower limb;
  a second compression portion for a portion of the foot comprising one or more bladders for applying pressure to the arch of the foot;
  a third compression portion comprising an inner wall and an outer wall forming one or more bladders being positioned so that a first bladder portion focuses compression on a first part of the posterior portion of the heel of the foot and a second bladder portion focuses compression on a second part of the posterior portion of the heel of the foot, wherein the first bladder portion is separated from the second bladder portion by spacers between the inner and outer walls, wherein the compression device is devoid of material at an open area so that the user places the plantar portion of the heel at the bottom of the foot in the open area when the compression device is being applied to the foot such that the compression device does not cover at least a part of the plantar portion at the bottom of the heel, and wherein the second compression device is configured such that the compression device does not cover the ball of the foot when the compression device is applied to the foot;
  at least one channel configured to deliver fluid to each of the first, second, and third compression portions; and
  a controller coupled to the channels that controls the flow of the fluid to the first, second, and third compression portions.

19. The compression device of claim 18, wherein the compression device comprises an inelastic fabric.

20. The compression device of claim 18, wherein the one or more bladders of the third compression portion comprises at least one bladder comprising an outer wall joined to an inner wall which contacts the foot in use, the at least one bladder being provided with separation apparatus to separate the walls to create a path for fluid flow into and out of the at least one bladder.

21. The compression device of claim 18, wherein the inner and outer walls of at least one bladder of the one or more bladders of the third compression portion are selectively welded to limit the inflation of the at least one bladder in certain areas so that the pressure applied by the at least one bladder is focused on selected areas of the foot.

22. The compression device of claim 18, wherein the first bladder portion and the second bladder portion provide compression on the posterior portion of the heel of the foot in the areas between malleoli and an Achilles tendon on either side of the heel, respectively.

23. The compression device of claim 18, wherein, when in use, the at least one channel of the second compression portion runs across at least a portion of the posterior portion of the heel between the one or more bladders of the second compression portion and the one or more bladders of the third compression portion.

* * * * *